United States Patent
Lohrengel et al.

(10) Patent No.: US 7,713,371 B2
(45) Date of Patent: May 11, 2010

(54) METHOD AND DEVICE FOR APPLYING A FLAT MATERIAL WEB SECTION

(75) Inventors: Armin Lohrengel, Steinheim (DE); Ralf Sprick, Heidenheim (DE); Bernd Frank, Steinheim (DE)

(73) Assignee: Paul Hartmann AG, Heidenheim (DE)

( * ) Notice: Subject to any disclaimer, the term of this patent is extended or adjusted under 35 U.S.C. 154(b) by 932 days.

(21) Appl. No.: 10/582,634

(22) PCT Filed: Dec. 8, 2004

(86) PCT No.: PCT/EP2004/013922

§ 371 (c)(1),
(2), (4) Date: Jun. 12, 2006

(87) PCT Pub. No.: WO2005/065617

PCT Pub. Date: Jul. 21, 2005

(65) Prior Publication Data

US 2007/0157778 A1    Jul. 12, 2007

(30) Foreign Application Priority Data

Dec. 30, 2003   (DE) .............................. 103 61 856

(51) Int. Cl.
  *B29C 65/00* (2006.01)
  *B32B 38/04* (2006.01)
(52) U.S. Cl. ...................... 156/256; 156/250; 156/510; 156/516; 156/517
(58) Field of Classification Search ................ 156/250, 156/256, 269, 270, 510, 516, 517, 519, 521, 156/581, 582; 604/385.14, 385.1, 385.04
See application file for complete search history.

(56) References Cited

U.S. PATENT DOCUMENTS 3,728,191 A * 4/1973 Wierzba et al. ............. 156/265

(Continued)

FOREIGN PATENT DOCUMENTS

EP        0 869 755        10/1998

(Continued)

*Primary Examiner*—Mark A Osele
*Assistant Examiner*—Christopher C Caillouet
(74) *Attorney, Agent, or Firm*—Paul Vincent

(57) ABSTRACT

The invention relates to a method for applying flat material web sections (28) to a first flat web of material (6) which is displaced in the direction of the machine having a first web speed during the production of hygiene articles or medical articles. The dimensions of the flat material web sections (28), in the direction of the machine, are smaller than the measurements of the articles which are to be produced. The flat material web sections (28) of an endless web (8) are separated in the cut-and-place method and are arranged on the first flat material web (6). The endless web (8) is fed at a second web speed to a second cutting station in the direction of a cutting roller (18). According to the inventive method, a front section (26) of the endless web (8) is applied against a surface section (24) of an anvil roller (22) which co-operates with the cutting roller (18), the surface section being curved less than the periphery (34) of the anvil roller (22). The front section (26) is cut in the endless web (8) in order to form the flat material web section (28) and each cut flat material web sections (28) is accelerated in a slip-free manner by the anvil roller (22).

27 Claims, 6 Drawing Sheets

U.S. PATENT DOCUMENTS

| | | | | |
|---|---|---|---|---|
| 4,237,890 A | * | 12/1980 | Laplanche | 604/390 |
| 4,767,487 A | | 8/1988 | Tomsovic | |
| 6,319,347 B1 | * | 11/2001 | Rajala et al. | 156/164 |
| 6,630,096 B2 | | 10/2003 | Venturino | |
| 6,814,217 B2 | * | 11/2004 | Blumenthal et al. | 198/459.8 |
| 6,827,893 B2 | * | 12/2004 | Clune | 264/129 |
| 2004/0194260 A1 | * | 10/2004 | Wendelstorf et al. | 24/442 |

FOREIGN PATENT DOCUMENTS

| | | |
|---|---|---|
| EP | 0 943 305 | 9/1999 |
| EP | 0 990 588 | 4/2000 |
| EP | 1 004 285 | 5/2000 |
| EP | 1 202 846 | 5/2002 |
| EP | 1 260 203 | 11/2002 |
| EP | 1 295 581 | 3/2003 |
| WO | WO 00/41664 | 7/2000 |
| WO | WO 03/024372 | 3/2003 |

* cited by examiner

METHOD AND DEVICE FOR APPLYING A FLAT MATERIAL WEB SECTION

This application is the national stage of PCT/EP2004/013922 filed on Dec. 8, 2004 and also claims Paris Convention priority of DE 103 61 856.2 filed on Dec. 30, 2003.

BACKGROUND OF THE INVENTION

The present invention concerns a method for applying flat material web sections onto a first flat material web moving in a machine direction at a first web speed during the production of hygiene articles or medical articles, wherein the extent of the flat material web sections in the machine direction is smaller than the dimension of the articles to be produced, wherein the flat material web sections are separated from an endless web using a "cut-and-place" procedure and are disposed onto the first flat material web, wherein the endless web is supplied towards a cutting roller of a cutting station at a second web speed. The first flat material web may also be a series of discrete articles. The invention also concerns a device for performing such a method, comprising a cutting roller and an anvil roller cooperating therewith.

The flat material web sections to be applied may e.g. be closing straps in the form of adhesive tape sections or sections comprising mechanical closing elements, or wound supports or gripping elements of bandaging materials, in particular adhesive bandages.

The articles to be produced, e.g. hygiene articles, such as diapers or diaper pants, are separated in sections from the preferably endless first flat material web moving in the machine direction. In order to produce these articles in an economic fashion, the flat material web sections to be applied are also separated from an endless web using the "cut-and-place" procedure and are disposed on the first flat material web, moving in the machine direction. Since the longitudinal extension of the flat material web sections to be applied is much smaller than the longitudinal extension of the article being produced, the first web speed of the first flat material web is faster than the second web speed with which the endless web is supplied to form the flat material web sections.

The following detailed problems arise:

When the endless web, which is supplied at a lower speed, is susceptible to slippage on an anvil roller, the endless web is subjected to abrasive wear. The peripheral speed of the anvil roller is many times higher, often up to 30 times higher, than the speed of the endless web in this contact area. Abrasion of the endless web soils the production device, and also transfers dirt particles onto the articles to be produced.

In particular, when adhesive coatings are used in the endless web, parts of the adhesive formed or sheared off during cutting, deposit on the anvil roller and are distributed about the overall periphery of the anvil roller due to the slippage of the endless web. They are also transported to the article to be produced via the flat material web sections being separated.

When flat material web sections are cut off from the endless web at relatively low speeds, and are then accelerated to a higher speed to be applied onto the first flat material web, one faces the problem that inertial masses must be accelerated and decelerated with high frequency. When relatively bending-resistant materials are used to form the flat material web sections, in particular, materials which are folded several times of top of each other, the reduction of the roller diameters in order to reduce the moved masses is problematic, since in this case, the bending-resistant materials and flat material web sections separated therefrom can hardly be kept on the surface of the anvil roller or other transport rollers. This would cause economically unacceptable disturbance of the production process.

For this reason, it has not been possible to find a satisfactory solution for the above-mentioned problems up to now.

It is therefore the underlying purpose of the present invention to provide a method and a device for performing the method, which permit application of flat material web sections onto a first flat material web extending in a machine direction to ensure economic production with high processing stability and which are not impaired by any of the above-mentioned problems.

SUMMARY OF THE INVENTION

This object is achieved in accordance with a method of the above-mentioned type in that a front section of the endless web is disposed against a surface section of an anvil roller cooperating with the cutting roller, wherein the surface section has a smaller curvature than the periphery of the anvil roller, the front section being cut off from the endless web to form the flat material web section, wherein each cut-off flat material web section is accelerated by the anvil roller without slippage.

In accordance with the inventive method, a front section of the endless web, which is directly separated from the endless web for forming the flat material web section being applied, is only slightly curved when disposed on the surface of the anvil roller, since this surface is less curved than a theoretical, cylindrical periphery of a cylindrical anvil roller. In accordance with the invention, the curvature of this surface section of the anvil roller and thereby the curvature of the section of the endless web disposed against it, is smaller than the curvature of a periphery of the anvil roller. The periphery of the anvil roller in the present case means the circular cross-section or the cross-section of a theoretical cylindrical jacket surface described by the point of the above-mentioned surface area of the anvil roller which has the largest separation from the axis of rotation of the anvil roller.

If, according to one embodiment of the invention, the above-mentioned surface section of the anvil roller describes a circular shape, viewed in cross-section, the radius of curvature of this circular shape is larger than the radius of the periphery of the anvil roller. The surface section of the anvil roller must not necessarily be circularly curved (this is only one special case for a curved surface). It may e.g. follow any polynomial curve shape or comprise flat surface sections forming a polygonal shape. In the limiting case, the surface section may also have an infinite radius of curvature, i.e. be flat.

The invention is particularly advantageous in many ways. The flat material web section to be applied may be less curved for a given size or diameter of the anvil roller. In other words, for a given minimum possible curvature of the flat material web section, smaller anvil roller diameters can be used. In the latter case, the mass of the anvil roller can be reduced which again promotes realization of dynamic acceleration and deceleration processes.

In a preferred further development of the invention, the flat material web section is accelerated after separation from the endless web in such a manner that it is applied to the first flat material web at substantially the first web speed. This acceleration process can be performed by the above-mentioned anvil roller alone or by one or more downstream transport rollers to which the respective flat material web section is transferred.

The front section of the endless web, which forms the flat material web section after separation from the endless web, is advantageously suctioned against the surface section of the anvil roller through underpressure.

As mentioned above, the angular velocity of the anvil roller is advantageously controlled in a periodically varying fashion.

When the front section of the endless web is received in cooperation with the cutting roller, the angular velocity of the anvil roller is advantageously low and preferably substantially corresponds to the supply speed of the endless web, i.e. the second web speed. The anvil roller and the flat material web section are highly accelerated preferably substantially directly after cutting off the flat material web section from the endless web. In a feasible and advantageous manner, the anvil roller accelerates the flat material web section to a peripheral or web speed which corresponds substantially to the first web speed. It would, however, also be feasible to provide a further transport roller or several transport rollers which perform the final acceleration of the flat material web section to the final first web speed. Moreover, use of a counter pressure roller in cooperation with an application roller which may be formed directly by the anvil roller is recommended for applying the flat material web section onto the first flat material web. The pressure roller rolls on the surface of the flat material web on the side of the flat material web facing away from the application roller and forms a counter bearing during application of the flat material web section onto the first flat material web.

It has turned out to be advantageous when the surface speed of the application roller, in particular, the anvil roller, and therefore the speed of the flat material web section substantially corresponds to the web speed of the first flat material web during application. In consequence thereof, the following should be noted: Due to the inventive small curvature of the surface section of the anvil roller and therefore the curvature of the flat material web section, which both differ from the curvature of the theoretical periphery of the anvil roller, the angular velocity of the anvil roller must be periodically changed during application to ensure that the web speed of the flat material web section is preferably constant over the entire phase of application, and preferably substantially corresponds to the first web speed. The periodic control of the angular velocity of the anvil roller is individually defined by the actual geometry of the surface section against which the flat material web section is applied.

An advantageous further development of the inventive idea proposes control of the angular velocity of the anvil roller during receiving and cutting off the flat material web section in such a manner that the resulting speed of the flat material web section corresponds to the second web speed, i.e. the supply speed of the endless web. Since the geometry of the surface section is not circular around the center of rotation of the anvil roller, the speed of rotation of the anvil roller must again be periodically controlled.

The present invention has turned out to be particularly advantageous in connection with flat material web sections or endless webs which are folded, in particular in the shape of a Z, about an axis or several axes extending in their longitudinal direction. The present invention proves to be particularly advantageous due to this Z-shaped folding which may advantageously be used for applying closing elements for disposable absorbent hygiene articles, since these endless webs or flat material web sections which are folded once or several times on top of themselves, have a higher bending resistance than single layer materials. For this reason, it is much more difficult to apply them to curved surfaces, in particular, to fix or suction them for transport purposes in fast-running production systems. When these flat material web sections, which are folded once or several times, are excessively curved during processing possible welding, gluing or perforation points, which detachably hold the folded web sections together, may be released. This disturbs the production process, since the above-mentioned means are intended to hold the folded web sections together in abutment, if possible, until use.

The above-mentioned object is also achieved by a device having the features of claim 11. This inventive device is characterized in that the anvil roller comprises a surface section which cooperates with the flat material web section to be separated and is less curved than the periphery of the anvil roller. The term periphery of the anvil roller is again defined as described above.

The surface section may, in particular, be cylindrically curved. In this case, its radius of curvature is larger than the radius of curvature of the periphery of the anvil roller. The radius of curvature of the surface section is preferably 50 to 250 mm, in particular 65 to 200 mm, in particular 80 to 150 mm, and preferably 90 to 120 mm.

The radius of curvature of the surface section of a further development of the invention is at least 1.5 times, in particular at least 1.7 times, in particular at least 1.8 times, and in particular at least 1.9 times, and preferably at least 2 times the radius of the periphery of the anvil roller.

In accordance with a preferred embodiment of the inventive device, the radius of the periphery of the anvil roller is 25 to 75 mm, in particular, 35 to 65 mm, and preferably 42 to 52 mm.

The cutting roller has at least two, preferably at least three knives disposed on its periphery. These knives may advantageously be held on the cutting roller in a resilient manner. The knives may be resiliently arranged in any fashion. According to a preferred embodiment, the roller comprises a curved, in particular U-shaped or S-shaped holding arm to which the knives can be mounted in a rigid, i.e. non-resilient manner, wherein the holding arm itself is radially resilient.

In a further particularly advantageous embodiment, the anvil roller is as lightweight as possible. This can be achieved e.g. in that the roller is radially recessed between peripheral surface sections for the abutment of the flat material web sections being applied, preferably proximate to an inner hub of the anvil roller. It has turned out to be advantageous for the anvil roller to comprise one single surface section for receiving the flat material web section, which spans approximately 45° to 120°, in particular 80° to 110° in the peripheral direction. As indicated above, the inventive device advantageously comprises a drive control means for periodically changing the angular velocity of the cutting roller and the anvil roller. The control parameters are thereby determined in dependence on the geometry of the rollers and the surface areas for receiving the flat material web sections in such a manner that desired speeds are reproducibly achieved during transfer of a flat material web section and during application of the flat material web section onto the first flat material web.

The inventive device is preferably designed in such a manner that the first web speed is at least 50 m/min and up to 400 m/min.

The second web speed at which the endless web is supplied for forming the flat material web sections to be applied depends on the differences between the section length of the flat material web section to be applied and the length of the article to be produced, and is preferably 5 to 80 m/min.

Preferred dimensions of the articles to be produced and of the flat material web sections to be applied can be extracted from the further claims.

BRIEF DESCRIPTION OF THE DRAWING

Further features, details and advantages of the invention can be extracted from the appended claims and the drawing and the following description of the inventive method and schematic representation of the inventive production device, and of an article to be produced.

DESCRIPTION OF THE PREFERRED EMBODIMENT

Figure 1:
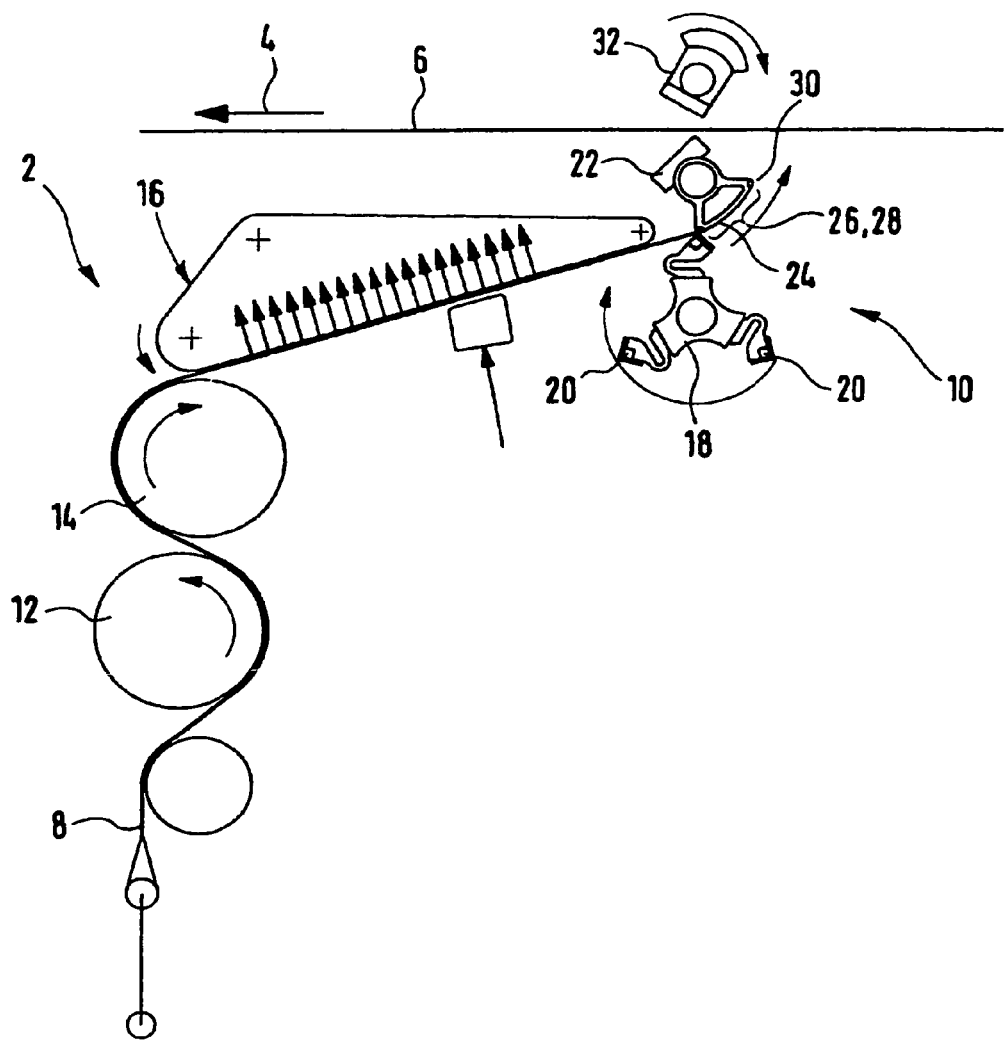
FIG. 1 shows a schematic view of an inventive device for applying flat material web sections onto a fast running flat material web.

FIG. 1 shows a device, designated in total with reference numeral 2, for applying a flat material web section to be described below, onto a first flat material web 6 which is moving in a machine direction 4 at a continuous, high speed. This first flat material web 6 may e.g. be a web for producing absorbent hygiene articles which are separated from the first flat material web as individual longitudinal sections. It may, however, also be a medical article, such as bandaging materials, in particular adhesive bandages.

FIG. 1 also schematically shows an endless web 8 which is unrolled from a roll (not shown) and is supplied, at a second web speed, to a cutting station, designated in total with reference numeral 10. This supply is realized via a so-called loop drive in the form of two transport rollers 12 and 14 and a suction belt drive 16. The endless web 8 is thereby supplied without slip in the direction towards the cutting station 10.

The cutting station 10 comprises a cutting roller 18 with at least two, in the present case, three, cutting knives 20. An anvil roller 22 is also provided, comprising a surface section 24 which cooperates with a front section 26 of the endless web 8 and the cutting knives 20. During supply of the endless web 8, the front section 26 of the endless web 8 is transported to the cutting station 10. The front section 26 is thereby applied against the surface section 24 of the anvil roller 22 and suctioned to the surface section 24 through underpressure. Due to the opposite drives of the cutting roller 18 and anvil roller 24, the knife 20 trailing in the direction of rotation cuts off the front section 26 from the endless web 8 such that the front section 26 abutting the surface section 24, forms a separated flat material web section 28 which is immediately highly accelerated by the anvil roller 22. In the present case, the anvil roller 22 accelerates the flat material web section 28 substantially from the second web speed of the endless web 8 to preferably substantially the first web speed of the first flat material web 6. In accordance with a preferred embodiment of the invention and with reference to FIG. 1, the anvil roller 22 is periodically accelerated and delayed in such a manner that the front end 30 of the flat material web section 28, viewed in the direction of rotation, reaches the first web speed of the first flat material web 6 at the "12 o'clock position". In a further development of the invention, the angular velocity of the anvil roller 22 is controlled in such a manner that during the entire application process of the flat material web section 28 onto the first flat material web 6, the web speed of the flat material web section 28 preferably always corresponds to the first web speed.

During application of the flat material web section 28 onto the first flat material web, the anvil roller 22 cooperates with a pressure roller 32 which is provided on the side of the first flat material web 6 facing away from the anvil roller 22 and is driven in an opposite direction with respect to the anvil roller 22, but preferably synchronous thereto.

Figure 2:
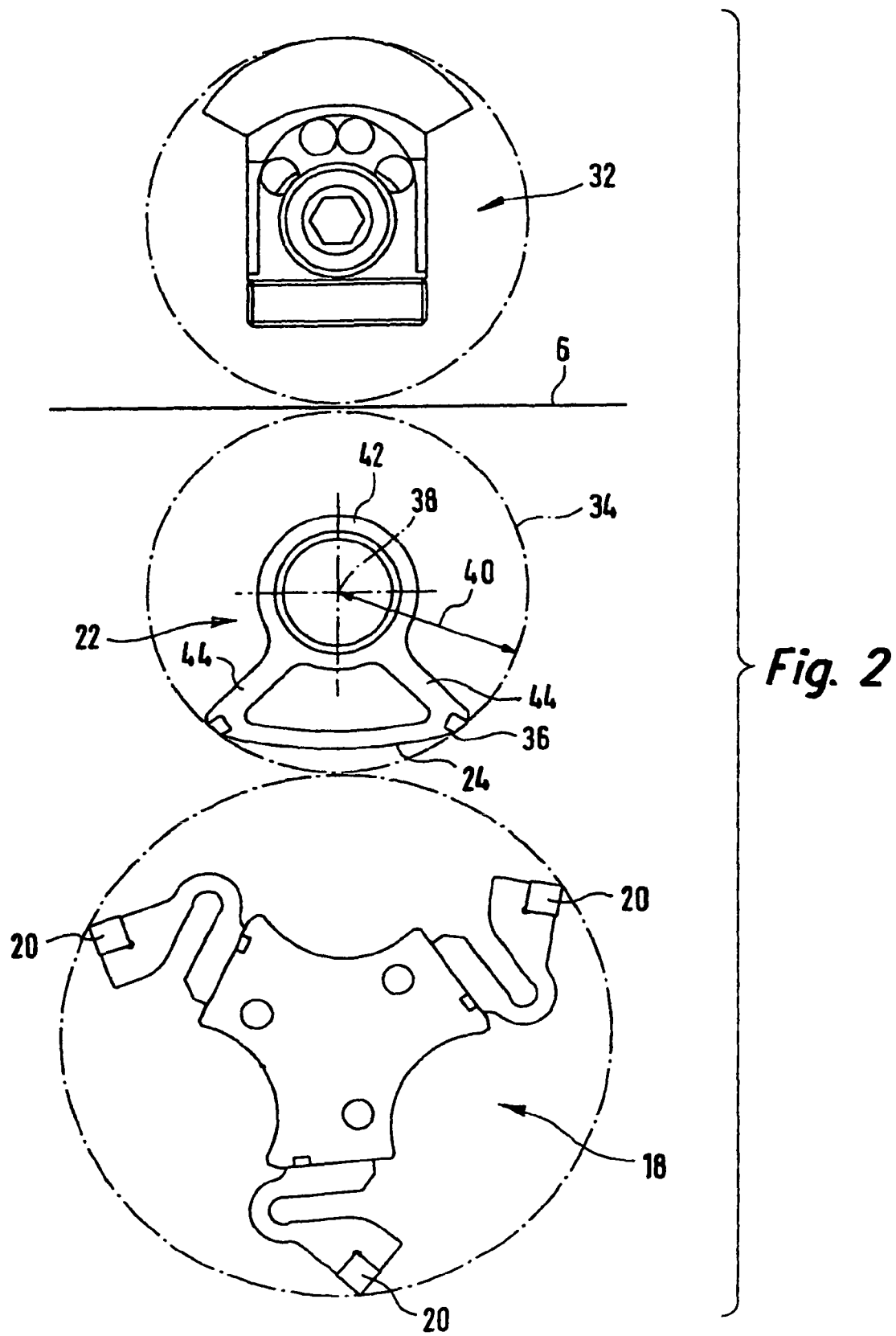
FIG. 2 shows a schematic view of a cutting roller, an anvil roller and a pressure roller of the inventive device.
Figure 3:
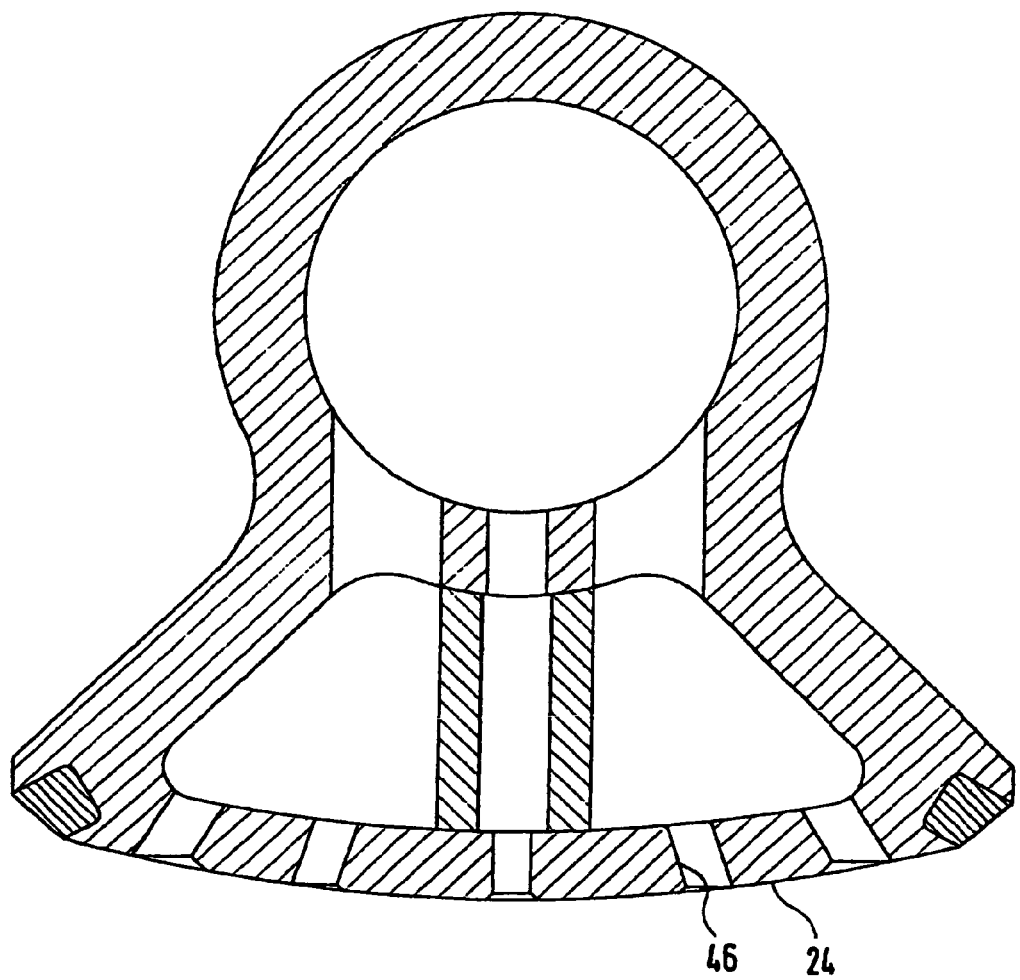
FIG. 3 shows a sectional view of the inventive design of an anvil roller.

FIG. 2 shows the cutting roller 18, the anvil roller 22 and the pressure roller 32. The curvature of the surface section 24 of the anvil roller is much smaller than the curvature of the periphery 34 of the anvil roller 22 which is formed by the circular path of a radially outer point 36 of the surface section 24 during its motion about the point of rotation 38 of the anvil roller 22. When the surface section 24 forms a section of a cylinder jacket surface, i.e. describes a path of a circular cross-section, its radius of curvature is much larger than the radius of curvature 40 of the periphery 34. In accordance with the invention, a front section 26 of the endless web 8 which is applied against the surface section 24, and is preferably suctioned, is much less curved than would be the case if the anvil roller 22 had a cylindrical periphery. Despite the small curvature, in particular, despite the very large radius of curvature of the surface section 24, it is nevertheless advantageously possible to achieve a relatively compact design for the anvil roller 22 with a peripheral radius 34 of preferably 2 to 75 mm. The weight of the anvil roller 22, i.e. the inertial mass, which must be overcome during dynamic acceleration and deceleration processes is therefore small and manageable. The anvil roller 22 is also radially recessed (FIG. 2) except for the area forming the surface section 24, which permits further mass reduction. The anvil roller 22 consists substantially of a hub region 42 surrounding a drive shaft and two struts 44 extending therefrom in a substantially radially outward direction, which bear the surface section 24. The detailed view of FIG. 3 shows openings 46 terminating in the surface section 24, which can be loaded from a radially inner direction with underpressure to suction the front section 26 or the flat material web section 28 against the surface section 24.

Figure 4:
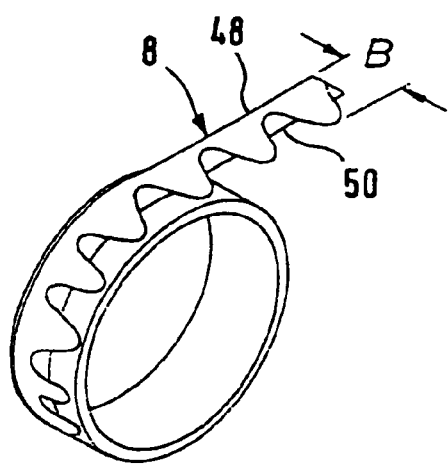
FIG. 4 shows a perspective view of an endless web which can be unrolled from a roll, for forming flat material web sections to be applied.
Figure 5:
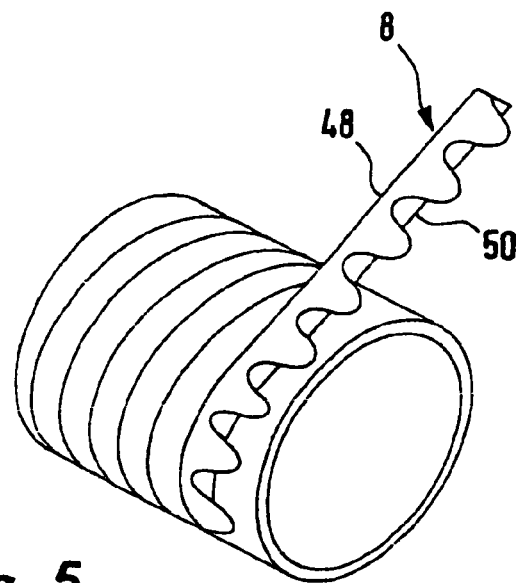
FIG. 5 shows a perspective view of an endless web which is helically wound.

FIGS. 4 and 5 show perspective views of the endless web 8 which can be unrolled from a roll to be supplied to the inventive device 2 of FIG. 1. The winding of the FIG. 5 has the shape of a helix. One can see that the endless web 8 is folded about an axis 48 extending in the longitudinal direction. Folding in a Z-shape and wrapping around a further longitudinal axis 50 is also possible.

Figure 6:
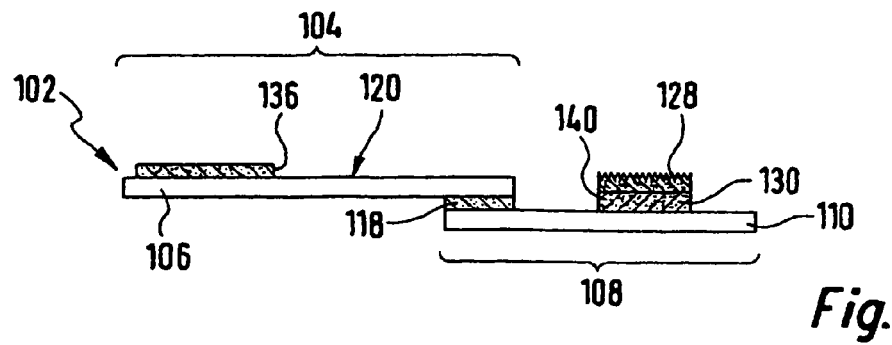
FIG. 6 shows a top view of a flat material web section to be applied, in the form of a closing strap for an absorbent hygiene article.
Figure 7:
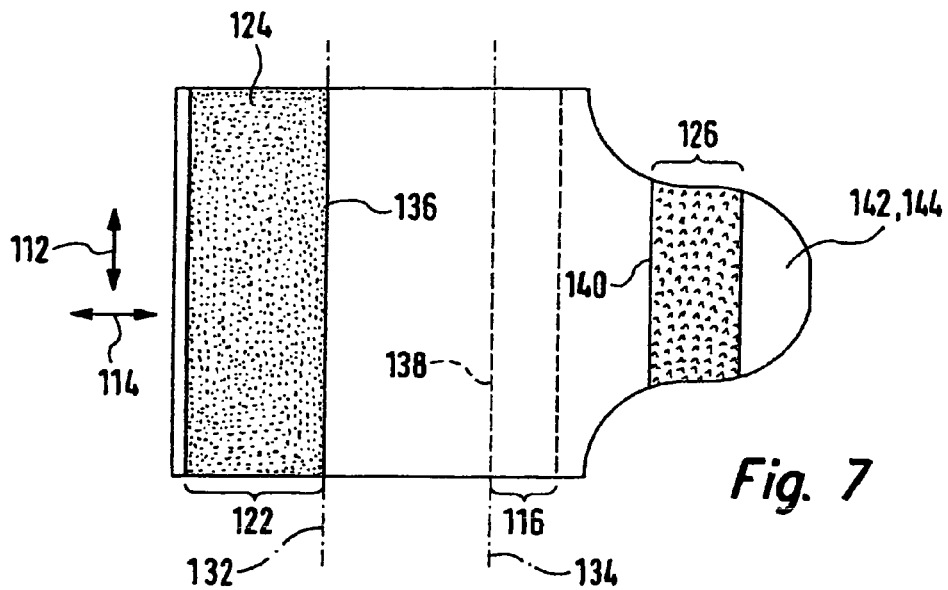
FIG. 7 shows a sectional view of the flat material web section of FIG. 2.
Figure 8:
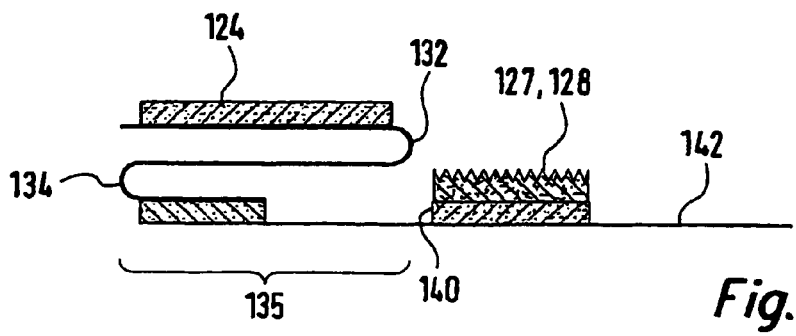
FIG. 8 shows a schematic view of the flat material web section of FIGS. 6 and 7 in a configuration folded in the shape of a Z.

FIGS. 6 through 8 show a fastening element which is designated in total with reference numeral 102. The fastening element 102 comprises a first section 104 of a first carrier layer 106 and a second section 108 of a second carrier layer 110.

The fastening element 102 is separated from the endless web 8 as a flat material web section 28, wherein the endless web 8 extends in the machine direction 112 indicated in FIG. 7. The second section 108 is disposed next to the first section 104 in a transverse direction 114, wherein the first section 104 and the second section 108 overlap each other in the present case to form an overlapping area 116, where the two sections 104, 108 are permanently connected to each other through an adhesive 118, via welding points, or in any other manner.

A first area 122 is provided on a first upper side 120 of the first section 104, which comprises an adhesive coating 24 for joining the fastening element to a hygiene article.

Fixing means 127 in the form of mechanically acting closing elements 128, preferably in the form of a hook-forming component of a hook/loop material are provided in a second area 126 of the second section 108, in particular, glued using an adhesive 130. The second area 126 is preferably provided on the same upper side 120 of the fastening element 102 as the first area 122.

First and second folding lines 132, 134 (corresponding to the folding lines 48, 50 of FIGS. 4 and 5) are moreover indicated in FIG. 7 and clearly shown in FIG. 8, about which the fastening element 102 is folded in a Z-shape in the longitudinal direction 112 of the endless web 8 to form the configuration 135 shown in FIG. 8. The first folding line 132 advantageously extends directly along a longitudinal edge 136 of the adhesive coating 124 in a first region 122. The second folding line 134 advantageously extends directly along the material transfer between the first and second sections 104 and 108, i.e. along an edge 138 of the overlapping area 116.

The second area 126 of the second section 108 is separated in a transverse direction 114 from the overlapping area 116 or from a different material transfer region between a first section 104 and a second section 108 to such an extent that it is located in the transverse direction 114 outside of the folded, Z-shaped configuration 135 of the fastening element 102 (FIG. 8) which may be advantageous in several ways. In the present case, a longitudinal edge 140 of the second area 126 facing the first section 104, and therefore the mechanically acting closing elements 128 nearly extend to the first folding line 136 in a transverse direction 114 when the configuration 125 is folded in a Z-shape. It would, however, also be feasible to position the second area 126 in the second section 108 in such a manner that the mechanically acting closing elements 128 or their longitudinal edge 140 have a separation of a few milimeters from the folded, Z-shaped configuration 135 of the fastening element.

It should be further mentioned that the first section 104 can be elastically stretched in the transverse direction 114 and the second section 108 cannot be substantially stretched in the transverse direction 114.

An adhesive coating of the first area 124 and the fixing means 127 in the second area 126 may be disposed in the longitudinal direction 112 continuously and endlessly onto a corresponding endless web 8 comprising the first carrier layer 106 and the second carrier layer 108. Correspondingly, the first and the second carrier layer 106, 108 are continuously connected to each other in the longitudinal direction 112 through an endless adhesive strip 118 or in a different manner. Simultaneous production of two mirror-inverted endless webs 8 which are offset by π/2 in the longitudinal direction, as disclosed e.g. in EP 0 669 121 A1, would also be feasible and advantageous.

As mentioned above, when the adhesive coating 124 of the fastening element 2 is disposed in the first area 122 onto a hygiene article, the second area 126 with the mechanically acting fixing means 127, 128 is disposed outside of the folded, Z-shaped configuration 35 and may thereby serve to fix the fastening element or the second section 108 to a textile surface of a hygiene article. This is explained below with reference to FIG. 9.

The fixing of the second section 108 to the hygiene article merely serves to fix the fastening element during production and packaging until the hygiene article is applied by a user, at which time this connection is released, if not earlier. A user's fingers grasp between the upper side of the hygiene article and a free end region 142 of the second section 108, which then serves as grasping area 144.

Figure 9:
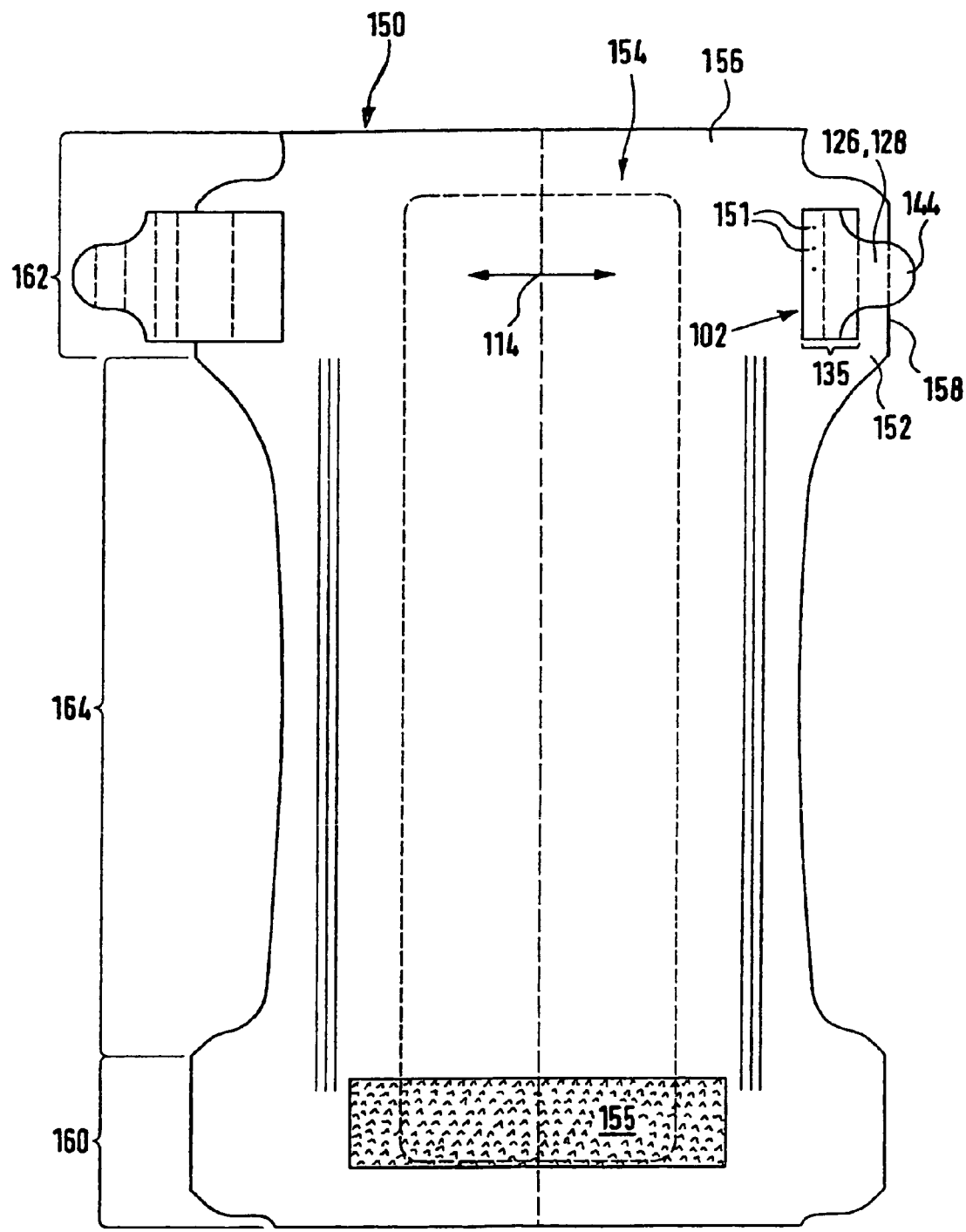
FIG. 9 shows a plan view of a hygiene article comprising a closing strap according to FIGS. 6 to 8.

FIG. 9 shows a plan view of an inventive diaper 150 with fastening elements 102 which are disposed on both sides in a rear area of the diaper 150 (described in connection with FIGS. 6 through 8). On the left hand side in FIG. 9, the fastening element 102 is unfolded and on the right hand side it is folded in a Z-shape. The first area 122 including rectangular adhesive coating 124 of the respective fastening element 102 are undetachably disposed onto a diaper outer side, i.e. onto an upper side 154 of a fluid-impermeable rear layer 156 of the diaper, facing away from the body when used as prescribed. The upper side 154 is formed by a textile-like non-woven material coating on a fluid impermeable sheet. The rear layer 156 is hence formed by a non-woven/sheet laminated material.

The fastening element 102 is disposed in the transverse direction 114 at a separation from a longitudinal edge 158 of the diaper 150 in the side flap or ear-shaped area of the diaper 150, such that only its grasping area 144 projects past the longitudinal edge 150 in the transverse direction 114. It is especially ensured that the second area 126 containing the mechanically acting closing elements 128 does not or only slightly project (at most by 5 mm) past the longitudinal edge 158 in the transverse direction when the fastening element is folded in a Z-shape. This prevents the closing elements 128 from getting hooked and possibly damaged when the side flaps or ear-shaped areas fold onto the covering layer facing the body.

The second area 126 with the closing elements 128 is located outside of the folded, Z-shaped configuration 135 and therefore abuts against the upper side 154 of the rear layer 156 of the diaper 150 (see FIG. 9 in connection with FIG. 8). The mechanically acting closing elements 128 are thereby detachably connected to the textile-like upper side 154 and hold the fastening element 102 in its folded, Z-shaped configuration 135. This prevents, in particular, the second section 108 including area 126 from becoming detached from the upper side 154. This improves the handling of the hygiene article after adding the fastening elements 102, which remain in their mounting position. The diaper 150 may be handled, in particular, folded, and stacked in a production machine and be supplied to a package.

The left hand side of FIG. 9 shows the unfolded state of the fastening elements 102. A user grasps the grasping area 144 and with the other hand he/she grasps around a longitudinal edge region 152 of the diaper 150 and pulls the two components apart. This releases the detachably adhering connection of the closing elements 128 to the textile-like upper side 154, and the fastening elements 102 are brought into the configuration shown in FIG. 9 on the left hand side, thereby unfolding the folded, Z-shaped configuration 135. The fastening elements can now be moved to a target area 155 in the form of a loop material, provided in the front area of the diaper 150, and be fastened to apply the diaper 150 to a user.

For further fixing of the fastening elements 102 in a folded, Z-shaped configuration 135, discrete fixing points, i.e. welding points 151, may be provided which detachably interconnect the Z-shaped layers of the fastening elements 2 which are folded on top of each other.

FIG. 9 also shows a front area 160, a rear area 162 and an intermediate crotch area 164 of the diaper 150.

We claim:

1. A method for applying a flat material web section onto a first flat material web, the first web moving at a first web speeds the method using a cut and place procedure to produce a hygiene or medical article, the flat web sections being shorter, in a machine direction, that an overall length of the produced articles, the method comprising the steps of:
   a) transporting, at a second web speed, an endless web towards a cutting roller of a cutting station, the endless web bearing a succession of flat material web sections;
   b) disposing a front section of the endless web against a surface section of an anvil roller cooperating with the cutting roller, the surface section having a radius of curvature of 50 to 250 mm, the radius of curvature of the surface section also being at least 1.5 times a radius of curvature of a periphery of the anvil roller;
   c) cutting-off the front section from the endless web to form the flat material web section;
   d) accelerating, using the anvil roller, the flat material web section, without slippage, towards the first web; and
   e) disposing the web section on the first web.

2. The method of claim 1, wherein the front section of the endless web is disposed against a surface section of the anvil roller having a cylindrical curvature and a radius of curvature which is larger than a radius of curvature of a periphery of the anvil roller.

3. The method of claim 1, wherein the flat material web section is applied to the first flat material web substantially at the first web speed.

4. The method of claim 1, wherein the front section of the endless web is suctioned against the surface section of the anvil roller using underpressure.

5. The method of claim 1, wherein an angular velocity of the anvil roller is controlled in a periodically changing manner.

6. The method of claim 5, wherein the angular velocity of the anvil roller or of a further transport roller is controlled during application of the flat material web section onto the first flat material web in such a manner that, during application, a speed of the flat material web section corresponds to the first web speed.

7. The method of claim 5, wherein, during receiving and cutting-off the flat material web section, the angular velocity of the anvil roller is controlled in such a manner that a speed of the flat material web section corresponds to the second web speed.

8. The method of claim 1, wherein a pressure roller is used on a side of the first flat material web facing away from the anvil roller to apply the flat material web section onto the first flat material web.

9. The method of claim 1, wherein the endless web is supplied in a folded state or in a folded Z-shape about an axis thereof extending in a longitudinal direction.

10. The method of claim 9, wherein folded web sections are detachably held together through welding, gluing, or perforation points.

11. A device for applying a flat material web section onto a first flat material web, the first web moving at a first web speed, the device using a cut and place procedure to produce a hygiene or medical article, the flat web sections being shorter, in a machine direction, that an overall length of the produced articles, the device comprising:

means for transporting, at a second web speed, an endless web towards a cutting roller of a cutting station; the endless web bearing a succession of flat material web sections;
   means for disposing a front section of the endless web against a surface section of an anvil roller cooperating with the cutting roller, the surface section having a radius of curvature of 50 to 250 mm, said radius of curvature of said surface section also being at least 1.5 times a radius of curvature of a periphery of the anvil roller;
   means for cutting-off the front section from the endless web to form the flat material web section;
   means for accelerating, using the anvil roller, the flat material web section, without slippage, towards the first web; and
   means for disposing the web section on the first web.

12. The device of claim 11, wherein said surface section is cylindrically curved.

13. The device of claim 12, wherein a radius of curvature of said surface section is 65 to 200 mm, 80 to 150 mm, or 90 to 120 mm.

14. The device of claim 12, wherein a radius of curvature of said surface section is at least 1.7 times, at least 1.8 times, at least 1.9 times, or at least 2 times a radius of curvature of a periphery of said anvil roller.

15. The device of claim 11, wherein a radius of a periphery of said anvil roller is 25 to 75 mm, 35 to 65 mm, or 42 to 52 mm.

16. The device of claim 11, wherein said cutting roller comprises at least two or at least three knives on a periphery thereof.

17. The device of claim 16, wherein said knives are resiliently held on said cutting roller.

18. The device of claim 11, wherein said anvil roller comprises one single surface section for receiving the flat material web section.

19. The device of claim 11, further comprising drive control means for periodically changing an angular velocity of said cutting roller and of said anvil roller.

20. The device of claim 11, wherein the first web speed is at least 50 m/mm to 400 m/mm.

21. The device of claim 11, wherein the second web speed is 5 to 80 m/mm.

22. The device of claim 11, wherein a length, in a machine direction, of the article to be produced is 30 to 150 cm or 45 to 110 cm.

23. The device of claim 11, wherein a section length of the flat material web section is 1 to 10 cm or 3 to 8 cm.

24. The device of claim 11, wherein the endless web supplied is folded or is folded with a Z-shape about at least one axis extending in a longitudinal direction thereof.

25. The device of claim 11, wherein a moment of inertia of said anvil roller is less than 0.0030 kg m$^2$ or less than 0.0025 kg m$^2$.

26. The device of claim 11, wherein a moment of inertia of said cutting roller is less than 0.0020 kg m$^2$ or less than 0.0016 kg m$^2$.

27. The device of claim 11, further comprising a pressure roller disposed on a side of the first material web opposite to said anvil roller and cooperating with said anvil roller during application of the flat material web section to the first material web, wherein a moment of inertia of said pressure roller is less than 0.0020 kg m$^2$ or less than 0.0016 kg m$^2$.

* * * * *